(12) United States Patent
Herrmann et al.

(10) Patent No.: US 8,810,259 B2
(45) Date of Patent: Aug. 19, 2014

(54) METHOD OF INSPECTION OF SEALED CAPSULES WITH A PROCESS OF DETERMINATION OF THE QUALITY OF THE SEAL AND RELATED EQUIPMENT FOR IN-LINE INSPECTION

(75) Inventors: Hans-Rainer Herrmann, Hamburg (DE); Tom Regina Augustinus Huysmans, Bornem (BE); Udo Schlemm, Hamburg (DE)

(73) Assignee: Capsugel Belgium NV, Bornem (BE)

( * ) Notice: Subject to any disclaimer, the term of this patent is extended or adjusted under 35 U.S.C. 154(b) by 198 days.

(21) Appl. No.: 13/509,313

(22) PCT Filed: Nov. 1, 2010

(86) PCT No.: PCT/IB2010/054931
§ 371 (c)(1),
(2), (4) Date: May 11, 2012

(87) PCT Pub. No.: WO2011/058475
PCT Pub. Date: May 19, 2011

(65) Prior Publication Data
US 2012/0229147 A1    Sep. 13, 2012

Related U.S. Application Data

(60) Provisional application No. 61/261,002, filed on Nov. 13, 2009.

(51) Int. Cl.
*G01N 27/00* (2006.01)
*G01R 27/26* (2006.01)
*G01N 22/04* (2006.01)
*A61J 3/07* (2006.01)
*G01N 33/15* (2006.01)

(52) U.S. Cl.
CPC .............. *A61J 3/072* (2013.01); *G01N 22/04* (2013.01); *G01N 33/15* (2013.01)
USPC ...................... 324/637; 324/557; 324/663

(58) Field of Classification Search
CPC ......... A61J 3/072; G01N 22/04; G01N 33/15; G01N 5/00
USPC .......................................... 324/637, 663, 557
See application file for complete search history.

(56) References Cited

U.S. PATENT DOCUMENTS

| 7,337,074 B2* | 2/2008 | Herrmann et al. ............. 702/23 |
| 2003/0138483 A1* | 7/2003 | Petriconi et al. ............. 424/456 |
| 2005/0110192 A1* | 5/2005 | Cade et al. ................... 264/275 |

* cited by examiner

*Primary Examiner* — Jermele M Hollington
*Assistant Examiner* — Farhana Hoque
(74) *Attorney, Agent, or Firm* — Klarquist Sparkman, LLP

(57) ABSTRACT

An exemplary embodiment of this invention relates to a method of inspection of a filled hard capsule sealed with a solvent sealing agent, including a process for determining the quality of the seal. The process may include: supplying a filled hard capsule sealed with a solvent sealing agent; supplying a microwave resonator wherein a measuring field having a resonance curve is generated; directing the capsule through the measuring field; measuring characteristics related to the modification of the resonance curve produced by the presence of the capsule in the measuring field, in comparison with a reference resonance curve corresponding to an empty state of the resonator; and using the measured characteristics to determine a value associated with the quality of the seal. Other exemplary embodiments of this invention relates to a method for sorting capsules on the basis of the result of the inspection method and to an associated equipment able to carry out such methods.

12 Claims, 2 Drawing Sheets

Figure 1:
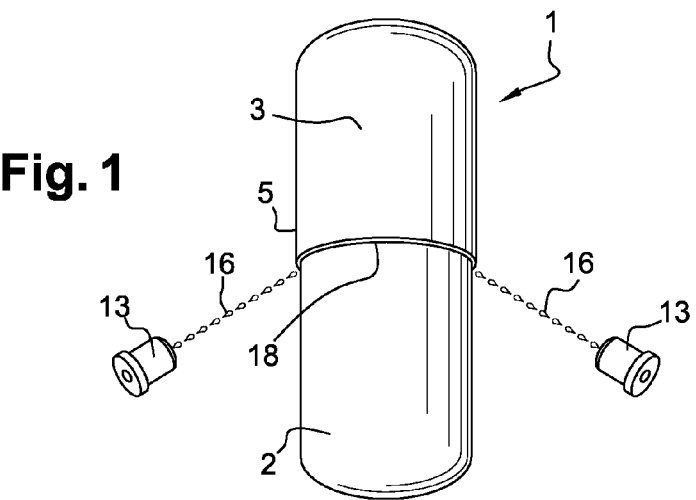

METHOD OF INSPECTION OF SEALED CAPSULES WITH A PROCESS OF DETERMINATION OF THE QUALITY OF THE SEAL AND RELATED EQUIPMENT FOR IN-LINE INSPECTION

This application is a national stage filing under 35 U.S.C. §371 of International Application No. PCT/IB2010/054931 filed on 1 Nov. 2010, which claims the benefit of priority to U.S. Provisional Application No. 61/261,002, filed 13 Nov. 2009. The contents of both applications are incorporated herein by reference in their entirety.

The invention relates to a method of inspection of a filled hard capsule sealed with a solvent sealing agent. In the context of the invention, the term "capsule" designates a container made of a pharmaceutically acceptable material and adapted to contain a dosage form to be ingested by a patient or user. Such a dosage form may include a pharmaceutically active ingredient or a dietary supplement.

The invention is intended to be used for inspecting hard capsules which are, more specifically but not exclusively, filled with a liquid. Hard capsules are typically made of two dip moulded parts, namely the body and the cap, made of gelatine or other suitable material. In a typical manufacturing process, the body and the cap once moulded are preassembled (or pre-closed) to be conveyed to a filling equipment wherein they are automatically separated, filled and closed. In the case of filling the capsules with a liquid, it is essential that the capsules are reliably sealed after filling in order to eliminate the risks of leakage.

It is known to provide a sealing equipment either separate from the filling equipment or integrated thereto, wherein the filled and closed capsules are sealed with the aid of a solvent sealing agent in the form of a fluid which is sprayed on the capsule such as to migrate by capillarity into the overlapping area of the body and the cap. The fluid then melts the capsule material in the overlap thus providing the sealing. Such sealing equipment and associated method are disclosed in e.g. WO 2004/082563, EP 116 743, EP 116 744, EP 180 543.

Although such equipments are able to operate at a high level of reliability, it is desirable to identify and eliminate every single defective capsule released from the equipment before it progresses further in the production line.

In this respect, the known visual methods are not satisfactory as they are only applicable for a sampled inspection.

It is also known from EP 1 669 755 to use microwaves to measure the mass and the moisture content of capsules. However, the disclosed methods and associated equipment give no indication of the quality of seal.

The quality of the seal is not only critical, especially when the capsule is filled with a liquid formulation, to the accuracy of the dose dispensed to the final user of the capsule, but also to the perceived overall quality of the capsule. An important problem with a defect of the seal is that a leakage caused by this defect may not only occur during the production process, but also later in the life of the capsule e.g. after packaging, whereby the defect may not be detected on the basis of a simple weight measurement of the content of the capsule.

Therefore, there is a need for a reliable method to inspect the quality of the seal of capsules, which can be used in a production line at a high throughput and easily combined with a method of determination of other critical characteristics of the capsules such as the weight.

This is achieved by the method of inspection of the invention, which includes a process for determining the quality of the seal, said process comprising supplying a filled hard capsule sealed with a solvent sealing agent;
supplying a microwave resonator wherein a measuring field characterized by a resonance curve is generated;
directing said capsule through the measuring field;
measuring characteristics related to the modification of the resonance curve produced by the presence of the capsule in the measuring field, in comparison with a reference resonance curve corresponding to an empty state of the resonator; and
using the measured characteristics to determine a value associated with the quality of the seal.

Advantageously, the method of the invention may have one or more of the following features:

the method further includes a step of using said measured characteristics to determine a seal area;
the method further includes a step of calculation of the mass of the capsule as a function of said measured characteristics;
the method further includes a step of calculation of the value associated with the quality of the seal as a function of at least one of said measured characteristics divided by said calculated mass;
said measured characteristics comprise the shift and the broadening of the resonance curve produced by the presence of the capsule in the measuring field.

According to a second aspect, the invention relates to a method for sorting capsules downstream a hard capsule sealing equipment, wherein each capsule is inspected with the aid of the aforementioned method and wherein said capsule is rejected for sealing defect if the value associated with the quality of the seal is lower than a predetermined threshold value.

According to a further aspect, the invention relates to an equipment for inspecting a hard capsule sealed with a solvent sealing agent, comprising a microwave resonator adapted to generate a measuring field characterized by a resonance curve and measure, when an object is directed through the measuring field, characteristics related to the modification of the resonance curve produced by the presence of the object in the measuring field, in comparison with a reference resonance curve corresponding to an empty state of the resonator;
means for singulating and directing individual capsules from a first section upstream the resonator to a second section downstream the resonator through the measuring field; and
calculation means adapted to determine a value associated with the quality of the seal as a function of said measured characteristics.

Advantageously, the equipment of the invention may include one or more of the following features:

said measured characteristics comprise the shift and the broadening of the resonance curve produced by the presence of the capsule in the measuring field;
the calculation means are adapted to calculate the mass of the capsule as a function of said measured characteristics;
the calculation means are adapted to calculate the value associated with the quality of the seal as a function of at least one of said measured characteristics divided by said calculated mass;
the calculation means comprise a comparator adapted to compare, for each capsule, the value associated with the quality of the seal with a predetermined threshold value and in that it further comprises rejection means adapted to divert the capsule from a normal path of capsules downstream the resonator if the value associated with the quality of the seal is lower than the predetermined threshold value;

the calculation means further comprise a comparator adapted to compare, for each capsule, (i) the value associated with the quality of the seal with a predetermined threshold value and (ii) the calculated value of the mass with a predetermined target range, and in that it further comprises rejection means adapted to divert the capsule from a normal path of capsules downstream the resonator if either (i) the value associated with the quality of the seal is lower than the predetermined threshold value or (ii) the calculated mass is out of the predetermined target range.

Figure 2:
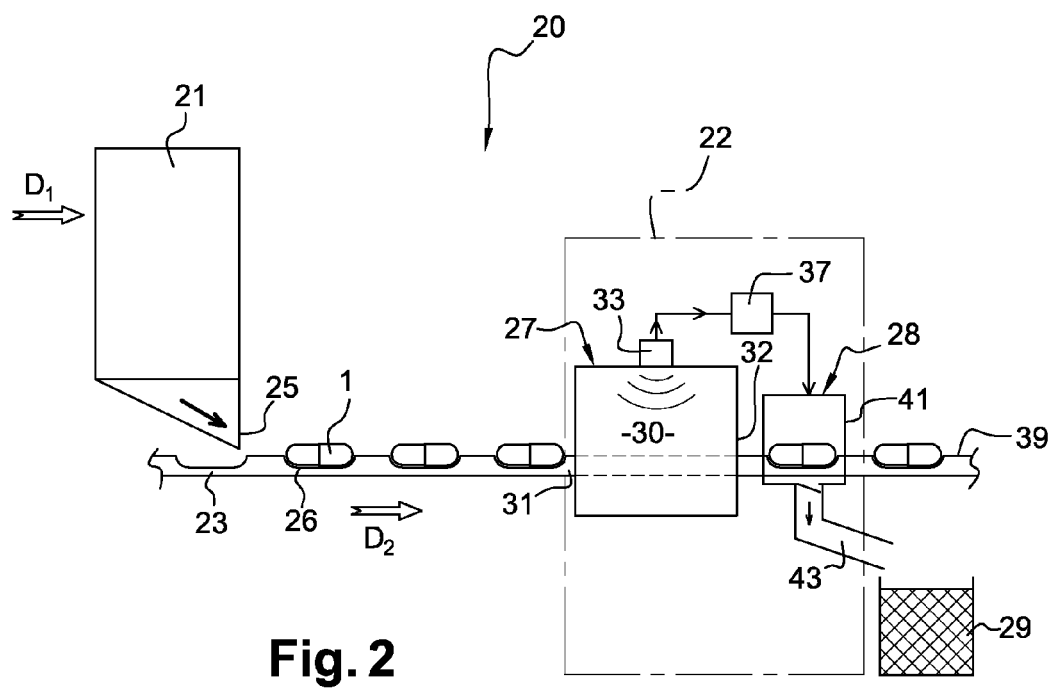
Figure 3:
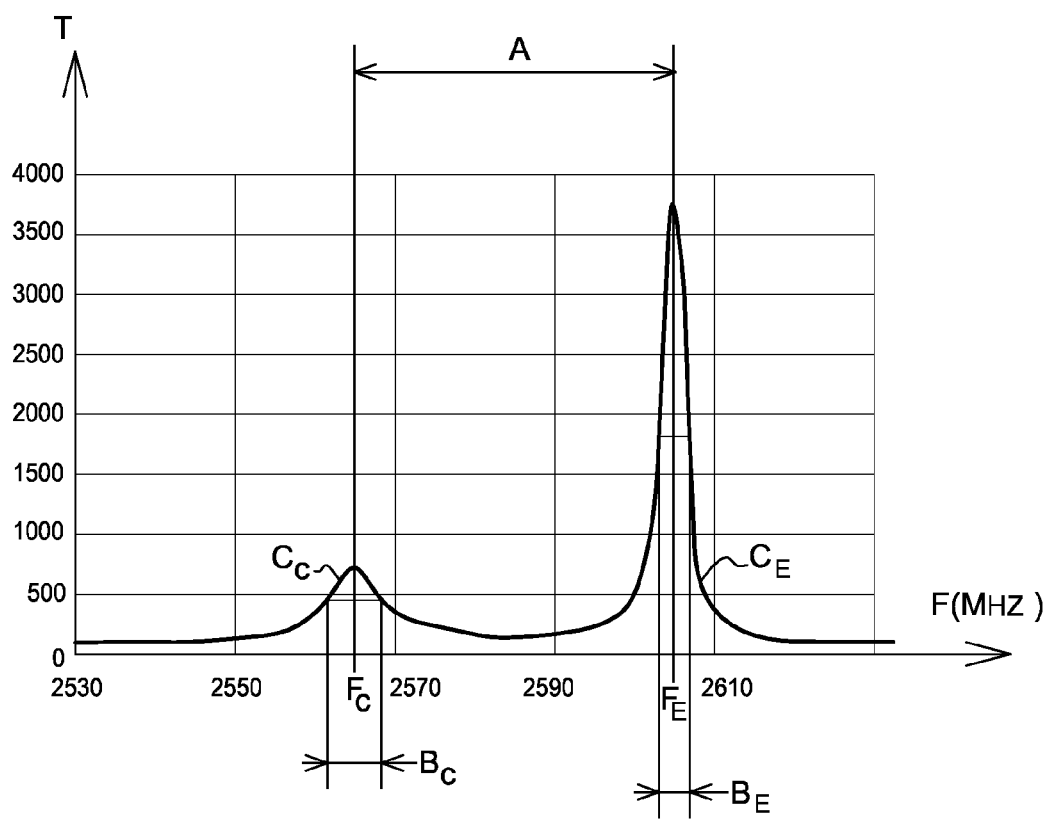

A preferred embodiment of the invention will now be described in more details, by way of example only, with reference to the accompanying drawings, in which:

FIG. 1 is a schematic enlarged perspective view of a hard capsule and sealing nozzles in a known process of sealing the capsule by projection of sealing liquid;

FIG. 2 is a schematic view of a section of a capsule production line, including a sealing equipment and an equipment for inspecting capsules according to the invention; and FIG. 3 is a graph illustrating the displacement of the resonant frequency and the broadening of the resonance curve, which are due to the influence of a capsule present in the resonator and which are measured and used in the method according to the invention.

FIG. 1 shows a typical hard capsule (or "hard-shell capsule") 1 comprises a hollow tubular body 2 and a hollow cap 3, each being typically made in one piece by moulding from a material such as gelatine or any other pharmaceutically acceptable material. For the sake of clarity, the represented capsule is not true to scale.

The body 2 and the cap 3 are adapted to be telescopically joined by partial insertion of the body 2 into the cap 3 until a fully closed, or engaged, final position and thus define a closed inner volume there between for accommodating a dosage. In this position, which is shown in FIG. 1, the body 2 and the cap 3 define an overlap region 5.

The herein described invention is of particular interest for capsules containing liquid dosages but it is also suitable for capsules with any other dosage form, such as powder.

FIG. 1 also illustrates the step of hermetically sealing such a capsule, wherein nozzles 13 are used to spray a sealing agent 16 towards the edge 18 of the cap. The sealing agent is a fluid containing a solvent, which may contain water. Some suitable examples of sealing agents can be found in U.S. Pat. No. 4,539,060.

Normally, the sealing agent sprayed onto the capsule is evenly distributed in the overlap region 5 by capillary effect and, in the case of a gelatine capsule, dissolves the contacting layers of the gelatine in the overlap of the body and the cap, thereby achieving the sealing of the capsule. The effect of the solvent containing sealing agent on a gelatine capsule is also described in U.S. Pat. No. 4,539,060.

With reference to FIGS. 2 and 3, a method and an equipment for inspecting such sealed capsules, in accordance to a preferred embodiment of the invention, will now be described.

FIG. 2 schematically illustrates a section 20 of a capsule production line including an equipment 21 for filling with liquid and sealing hard capsules continuously supplied by a manufacturing station (not shown) arranged upstream the equipment 21. The flow of capsules from the manufacturing station into the equipment 21 is represented by the arrow $D_1$. Such an equipment, designed as an integrated filling and sealing equipment or as distinct filling and sealing apparatuses, is known in the art and will not be described in details. It is just worth noting that the sealing of the capsules is preferably carried out in this equipment in accordance with the principles mentioned with reference to FIG. 1.

The section 20 also includes, downstream the filling and sealing equipment 21, an inspection equipment 22 according to the invention provided to inspect and sort the capsules supplied by the equipment 21. The flow of capsules 1 from the filling and sealing equipment 21 to the inspection equipment 22 is represented by the arrow $D_2$.

On FIG. 2, the general direction of the flow of capsules in the section 20 of production line is indicated by the arrows $D_1$ and $D_2$. The terms "upstream" and "downstream" in the whole description should be interpreted with reference to this general flow direction.

The section 20 further includes a conveyor 23 adapted to convey successive singulated capsules 1 from an outlet 25 of the equipment 21 into and across the inspection equipment 22. To this end, the conveyor may be formed by an endless belt provided with successive pockets 26 along the main direction of displacement $D_2$, said pockets being each adapted to accommodate a single capsule 1.

The inspection equipment 22 comprises a microwave resonator 27 able to carry out the inspection of the capsules and, downstream the resonator 27, rejection means 28 able to eliminate defective capsules. For example, the defective capsules are directed by the rejection means 28 into a bin 29 provided in the section 20 of the production line.

The resonator 27 includes a cavity 30 with an inlet 31 and an outlet 32 for the capsules, the inlet 31 corresponding to the inlet of the inspection equipment 22. It also includes a microwave measuring system 33 able to generate microwave signals in the cavity 30 at resonance frequencies with characteristic resonance curves, thus defining a measuring field, and to measure characteristics of the electromagnetic field as modified by the introduction of an object—in this case a capsule—in the cavity 30.

For example, the measuring system 33 may be of the type TEWS MW® 3011 manufactured by the Company TEWS.

The inspection equipment 22 is further provided with calculation means 37, which are connected, on the one hand, to the measuring system 33 and, on the other hand, to the rejection means 28.

From the input signals received from the measuring system 33, the calculation means 37 are adapted to calculate variables representative of certain properties of the capsule introduced in the cavity, as will be explained below.

The calculation means 37 are also adapted to control the rejection means 28, depending on estimated properties associated with the capsule, so as to divert said capsule from the normal path of the capsules downstream the resonator 27 and direct it into the bin 29. The normal path should be understood as the path defined by the conveyor 23 from the resonator 27, through a main outlet 39 of the inspection equipment 22, to a subsequent section of the production line, e.g. including a printing equipment or a packaging equipment.

For example, as illustrated on FIG. 2, the rejection means may have a blower 41 controlled by the calculation means 37 and a duct 43 designed to transfer the defective capsules blown away by the blower 41 from the conveyor 23 into the bin 29.

In another embodiment (not shown), the conveyor may be of the type "air conveyor" including a first tube-like guide upstream the cavity 30 to achieve air transportation of the capsules into the cavity and a second tube-like guide downstream the cavity to achieve air transportation of the capsules from the cavity 30.

Reference will now be made to FIGS. 2 and 3 to describe in more details the method of inspection according to the invention.

The method of inspection according to the invention carried out by the inspection equipment 22 includes a process of determination of the quality of the seal. This process is based on the assumption that, in a section directly downstream the sealing apparatus, the overall humidity of a capsule is determined by the quantity of sealing agent present on the capsule. Such assumption accurately reflects the reality in the most current conditions where the capsules are filled with a dosage form containing no solvent and where the amount of solvent of the dose is negligible compared to the amount of solvent provided by the sealing agent.

The process of determination of the quality of the seal is carried out on successive hard capsules 1 sealed with the solvent containing agent in the filing and sealing equipment 21 and continuously supplied to the inspection equipment 22 through the inlet 31 by the conveyor 23. In this process, the capsules are successively led through a measuring field generated in the cavity 30 of the microwave resonator 27, the measuring field in an empty state of the cavity being characterized by a certain resonance frequency $F_E$ and a characteristic resonance curve $C_E$.

In the illustrated embodiment, wherein a section of the conveyor extends across the cavity, the term "empty state" should be interpreted as a state wherein the pocket 26 enclosed in the cavity is empty, no capsule being thus present in the cavity. This configuration could also be depicted by the expression "empty pocket state".

If other types of conveyors are used, such as an air-conveyor, wherein the capsules are transported without guiding elements extending across the cavity, the "empty state" corresponds to a real empty state of the cavity, not only to a state with no capsule in the cavity.

In the context of the invention, the "empty state" of the resonator thus means:
- the real empty state if the capsules are transported without guiding elements, and
- the empty pocket state if the capsules are transported on a belt.

On FIG. 3, resonance curves $C_E$ and $C_c$, respectively in empty state of the cavity and in presence of a capsule, are shown in a graph with frequencies (in MHz) in abscissas and transmission ratios T in ordinates.

As illustrated on FIG. 3, the presence of a capsule 1 in the measuring field causes the resonance frequency to be shifted to a lower value $F_C$ and the resonance curve to be broadened $C_C$. The shift of the resonance frequency defines a first variable A which is measured by the measuring system 33. The broadening B of the resonance curve, which is the difference of the half-value widths $B_C$, $B_E$ respectively of the curve $C_C$ and the curve $C_E$, defines a second variable, also measured by the measuring system 33.

The calculation means 37 have a processor programmed to calculate a solvent value θ associated with the capsule, using the measured variables A, B. This solvent value θ is independent from the mass of the capsule and from the mass of the dose contained in the capsule and is calculated as a function of the first A and second B variables only.

According to a first embodiment, the solvent value is calculated using the relationship $$\theta = t_1 \cdot (B/A) + t_2$$

where $t_1$ and $t_2$ are predetermined calibration coefficients which are calculated during a calibration process. The calibration process will not be described in much details.

In line with the aforementioned assumption, the quality of the seal is reflected by the solvent value θ thus estimated. In the present determination process, a value representative of the quality of the seal is therefore determined as a simple function of the solvent value θ. The value representative of the quality of the seal is preferably proportional to the solvent value θ and most preferably equal to the solvent value θ.

The method of inspection according to the invention also comprises a step of calculation of the mass M of the capsule, which is carried out by the same equipment 22 using the same measured variables A, B. The processor of the calculation means 37 is thus also programmed to calculate the mass M with the aid of a relationship involving A and B as only variables.

In particular, the calculation of the mass M is achieved with the aid of the relationship:

$$M = b_1 \cdot A + b_2 \cdot B + b_3$$

wherein the coefficients $b_1$, $b_2$, $b_3$ are calibrations coefficients, preferably constant coefficients for capsules of a same bulk and of the same type, said coefficients being predetermined and stored in the calculation means 37.

According to a second embodiment, requiring the use of a resonator with three simultaneously excitable resonance modes, the variables A and B are acquired for each mode. The values thus obtained $A_1$, $A_2$, $A_3$ and $B_1$, $B_2$, $B_3$ are used to calculate the solvent value θ and the mass M as set forth below:

$$\theta = t_1 \cdot (B_1/A_1) + t_2 \cdot (B_2/A_2) + t_3 \cdot (B_3/A_3) t_4$$

$$M = k_1 \cdot A_1 + k_2 \cdot A_2 + k_3 \cdot A_3 + k_4 \cdot B_1 + k_5 \cdot B_2 + k_6 \cdot B_3$$

wherein $t_i$, i=1, ... 4 and $k_j$, j=1, ... 7 are predetermined calibration coefficients which are calculated during a calibration process.

According to a third embodiment, the value associated with the quality of the seal is either the transformed shift A' or the transformed broadening B', respectively obtained by the division of the shift A and the broadening B by the calculated mass M:

$$A' = A/M$$

$$B' = B/M$$

Alternatively, the value associated with the quality of the seal may be calculated as a function of both the transformed shift A' and the transformed broadening B'.

In this embodiment, the value associated with the quality of the seal is de-correlated from the filling level, due to the division of the measured variables A, B by the calculated mass M.

The calculation means 37 further include a buffer and a comparator. The buffer is able to momentarily store the characteristics of each capsule, i.e. the value associated with the quality of the seal θ (or A', B') and the mass M as estimated with the method of inspection. The comparator is adapted to compare, in a comparison step, these characteristics with predetermined values stored in the calculation means and return a defect value representative of either the absence of defect or the type of defect(s) found during the inspection, depending on the result of the comparison step.

More specifically, the predetermined stored values comprise a threshold value $\theta_0$ (or $A'_0$, $e'_0$) for the quality of the seal and a target range of values $[M_1, M_2]$ for the mass.

In case the estimated value θ (or A', B') associated with the quality of the seal of a capsule is lower than the threshold value $θ_0$ (or $A'_0$, $B'_0$) for the quality of the seal, then the comparator returns a value representative of a sealing defect on the capsule, which might reveal the absence of the seal or more generally an insufficient quantity of sealing agent.

In case the estimated mass M of the capsule is out of the target range $[M_1, M_2]$ i.e. lower than $M_1$ or higher than $M_2$, then the comparator returns a value representative of a mass defect on the capsule, which would generally reveal an unacceptably inaccurate dose contained in the capsule.

In case both the estimated value θ (or A', B') is lower than the threshold value $θ_0$ (or $A'_0$, $B'_0$) and the estimated mass M of the capsule is out of the target range $[M_1, M_2]$, then the comparator returns a value representative of both a sealing defect and a mass defect on the capsule.

In case both the estimated value θ (or A', B') is higher than the threshold value $θ_0$ (or $A'_0$, $B'_0$) and the estimated mass M of the capsule is within the target range $[M_1, M_2]$, then the comparator returns a value representative of a non-defective capsule.

It will be appreciated that, when the inspection is based on the transformed variables A', B', the associated threshold values $A'_0$, $B'_0$ are also independent from a target filling level. With this method, it is not only possible to separate well-sealed from poor-sealed capsules, but it is also possible to more precisely classify the quality of the seal of each capsule.

The calculation means 37 are adapted to control the rejection means 28 on the basis of the defect value returned by the comparator. If the defect value for an inspected capsule is different from the value representative of a non-defective capsule, then the rejection means 28 are activated so as to divert said capsule from the normal path and direct it into the bin 29, thereby sorting the capsules led through the inspection equipment 22 downstream the filling and sealing equipment 21. The non-defective capsules normally progress through the main outlet 39 of the inspection equipment further in the production line.

It will be appreciated that the invention provides reliable methods for in-line inspecting and sorting capsules, which can be carried out automatically and at high throughputs (e.g. 70 000 capsules/hour for one single line). The associated equipments can thus be integrated in production lines without reducing the throughput achieved by the upstream filling and sealing stations.

The invention claimed is:

1. Method of inspection of a filled hard capsule sealed with a solvent sealing agent, including a process for determining the quality of the seal, said process comprising:
   supplying a filled hard capsule sealed with a solvent sealing agent;
   generating a measuring field having a resonance curve with a microwave generator;
   directing said capsule through the measuring field;
   measuring characteristics related to a modification of the resonance curve produced by the presence of the capsule in the measuring field, in comparison with a reference resonance curve corresponding to an empty state of the resonator;
   determining a seal area using said measured characteristics; and
   determining a value associated with the quality of the seal using said measured characteristics.

2. Method according to claim 1 further including calculating a mass of the capsule as a function of said measured characteristics.

3. Method according to claim 2, further including calculating the value associated with the quality of the seal as a function of at least one of said measured characteristics divided by said calculated mass.

4. Method according to claim 1, wherein said measured characteristics comprise a shift and a broadening of the resonance curve produced by the presence of the capsule in the measuring field.

5. Method according to claim 1, further including sorting capsules downstream from a hard capsule sealing equipment, wherein said capsule is rejected for sealing defect if the value associated with the quality of the seal is lower than a predetermined threshold value.

6. Equipment for inspecting a hard capsule sealed with a solvent sealing agent, comprising:
   a microwave resonator adapted to generate a measuring field having a resonance curve and measure, when an object is directed through the measuring field, characteristics related to a modification of the resonance curve produced by the presence of the object in the measuring field, in comparison with a reference resonance curve corresponding to an empty state of the resonator;
   a delivery device for singulating and directing individual capsules from a first section upstream the resonator to a second section downstream the resonator through the measuring field; and
   a controller for calculating a value associated with a seal area as a function of said measured characteristics.

7. Equipment according to claim 6, wherein said measured characteristics comprise a shift and a broadening of the resonance curve produced by the presence of the capsule in the measuring field.

8. Equipment according to claim 6, wherein the controller is adapted to calculate a mass of the capsule as a function of said measured characteristics.

9. Equipment according to claim 8, wherein the controller is adapted to calculate the value associated with the seal area as a function of at least one of said measured characteristics divided by said calculated mass.

10. Equipment according to claim 8, wherein the controller further comprises a comparator adapted to compare, for each capsule,
    (i) the value associated with the seal area with a predetermined threshold value and
    (ii) the calculated value of the mass with a predetermined target range.

11. Equipment according to claim 10, wherein the controller further comprises a rejection device adapted to divert the capsule from a normal path of capsules downstream the resonator if either:
    (i) the value associated with the seal area is lower than the predetermined threshold value or
    (ii) the calculated mass is out of the predetermined target range.

12. Equipment according to claim 6, wherein the controller comprises a comparator adapted to compare, for each capsule, the value associated with the seal area with a predetermined threshold value and in that it further comprises a rejection device adapted to divert the capsule from a normal path of capsules downstream the resonator if the value associated with the quality of the seal is lower than the predetermined threshold value.

* * * * *